United States Patent
Janda et al.

(10) Patent No.: US 6,486,219 B1
(45) Date of Patent: Nov. 26, 2002

(54) METHANOL, OLEFIN, AND HYDROCARBON SYNTHESIS PROCESS

(75) Inventors: Gary F. Janda, Houston, TX (US); Keith H. Kuechler, Friendswood, TX (US)

(73) Assignee: ExxonMobil Chemical Patents, Inc., Houston, TX (US)

( * ) Notice: Subject to any disclaimer, the term of this patent is extended or adjusted under 35 U.S.C. 154(b) by 0 days.

(21) Appl. No.: 09/670,755

(22) Filed: Sep. 27, 2000

(51) Int. Cl.[7] ............... C07C 27/00; C07C 1/00
(52) U.S. Cl. ............ 518/706; 518/700; 518/702; 518/703; 518/704; 585/640
(58) Field of Search ............... 518/700, 702, 518/703, 704, 706; 585/640

(56) References Cited

U.S. PATENT DOCUMENTS

| | | | |
|---|---|---|---|
| 2,906,695 A | 9/1959 | Boston | 208/127 |
| 3,258,455 A | 6/1966 | Natta et al. | 260/93.7 |
| 3,305,538 A | 2/1967 | Natta et al. | 260/93.7 |
| 3,364,190 A | 1/1968 | Emrick | 260/93.7 |
| 3,645,992 A | 2/1972 | Elston | 260/80.78 |
| 3,647,682 A | 3/1972 | Rabo et al. | 208/120 |
| 3,888,896 A | 6/1975 | Espino et al. | 260/449.5 |
| 4,031,123 A | 6/1977 | Espino et al. | 260/449.5 |
| 4,076,698 A | 2/1978 | Anderson et al. | 526/348.6 |
| 4,243,691 A | 1/1981 | Mohlenkamp, Jr. et al. | 426/649 |
| 4,302,565 A | 11/1981 | Goeke et al. | 526/88 |
| 4,310,440 A | 1/1982 | Wilson et al. | 252/435 |
| 4,419,221 A | 12/1983 | Castagnos, Jr. et al. | 208/113 |
| 4,440,871 A | 4/1984 | Lok et al. | 502/214 |
| 4,499,327 A | 2/1985 | Kaiser | 585/640 |
| 4,613,721 A | 9/1986 | Kaiser | 585/643 |
| 4,659,685 A | 4/1987 | Coleman, III et al. | 502/214 |
| 4,677,242 A | 6/1987 | Kaiser | 585/638 |
| 4,677,243 A | 6/1987 | Kaiser | 585/638 |
| 4,752,651 A | 6/1988 | Kaiser | 585/640 |
| 4,861,743 A | 8/1989 | Flank et al. | 502/214 |
| 4,861,938 A | 8/1989 | Lewis et al. | 585/640 |
| 4,886,651 A | 12/1989 | Patel et al. | 423/359 |
| 5,095,163 A | 3/1992 | Barger | 585/640 |
| 5,096,684 A | 3/1992 | Guth et al. | 423/306 |

(List continued on next page.)

FOREIGN PATENT DOCUMENTS

| | | |
|---|---|---|
| AU | 199852747 | 8/1999 |
| DE | 3 524 890 | 7/1985 |
| DE | 3521304 A1 * | 12/1986 |
| EP | 060 103 | 9/1982 |
| EP | 096 996 | 12/1983 |
| EP | 0 359 841 | 11/1993 |
| EP | 0 640 559 | 6/1995 |

(List continued on next page.)

OTHER PUBLICATIONS

Blackwell et al., Solid–State NMR of Silicoaluminophosphate Molecular Sieves and Aluminophsophate Materials, J. Phys. Chem., vol. 92, pp. 3965–3970 (1988).

(List continued on next page.)

*Primary Examiner*—Jafar Parsa
(74) *Attorney, Agent, or Firm*—Paul T. LaVoie

(57) ABSTRACT

An improved method for the production of methanol and hydrocarbons from a methane-containing gas, such as natural gas. The improved method integrates a hydrocarbon synthesis unit with a methanol synthesis unit. The invention combines a syngas stream from a steam reformer, a syngas stream from an oxidation reformer and additional carbon dioxide to form an optimal syngas composition that is directed to a methanol synthesis reactor. The invention also integrates other process parameters and process components of a methanol and hydrocarbon synthesis process plant to effectively convert most of the carbon in the natural gas to commercial-value products. The invention is also directed to a method of making olefin from the methanol produced by the process of the invention.

21 Claims, 3 Drawing Sheets

U.S. PATENT DOCUMENTS

| | | | | |
|---|---|---|---|---|
| 5,126,308 | A | 6/1992 | Barger et al. | 502/214 |
| 5,157,181 | A | 10/1992 | Stine et al. | 585/329 |
| 5,177,114 | A | 1/1993 | Van Dijk et al. | 518/703 |
| 5,191,141 | A | 3/1993 | Barger et al. | 585/640 |
| 5,278,345 | A | 1/1994 | Janssen et al. | 585/640 |
| 5,475,182 | A | 12/1995 | Janssen | 585/640 |
| 5,496,859 | A | 3/1996 | Fong et al. | 518/703 |
| 5,714,662 | A | 2/1998 | Vora et al. | 585/640 |
| 5,714,663 | A | 2/1998 | Serrand et al. | 585/648 |
| 5,744,680 | A | 4/1998 | Mulvaney, III et al. | 585/640 |
| 5,856,585 | A * | 1/1999 | Sanfilippo et al. | 568/470 |
| 5,892,079 | A | 4/1999 | Wilson, Jr. | 556/11 |
| 5,904,880 | A | 5/1999 | Sun | 252/373 |
| 5,912,393 | A | 6/1999 | Barger et al. | 585/640 |
| 5,914,433 | A | 6/1999 | Marker | 585/313 |
| 5,927,063 | A | 7/1999 | Janda et al. | 60/39.02 |
| 5,932,512 | A | 8/1999 | Sun | 502/214 |
| 5,952,538 | A | 9/1999 | Vaughn et al. | 585/640 |
| 5,972,203 | A | 10/1999 | Smith et al. | 208/113 |
| 5,990,369 | A * | 11/1999 | Barger et al. | 585/640 |
| 6,005,155 | A | 12/1999 | Sun | 585/640 |
| 6,023,005 | A | 2/2000 | Lattner et al. | 585/639 |
| 6,040,264 | A | 3/2000 | Sun et al. | 502/214 |
| 6,046,371 | A | 4/2000 | Wu et al. | 585/638 |
| 6,051,745 | A | 4/2000 | Wu et al. | 585/638 |
| 6,051,746 | A | 4/2000 | Sun et al. | 585/639 |
| 6,057,261 | A | 5/2000 | Sun | 502/341 |
| 6,121,503 | A | 9/2000 | Janssen et al. | 585/640 |
| 6,121,504 | A | 9/2000 | Kuechler et al. | 585/640 |
| 6,137,022 | A | 10/2000 | Kuechler et al. | 585/638 |
| 6,147,126 | A | 11/2000 | DeGeorge et al. | 518/715 |
| 6,156,809 | A * | 12/2000 | Clark et al. | 518/719 |
| 6,166,282 | A | 12/2000 | Miller | 585/638 |
| 6,248,794 | B1 * | 6/2001 | Gieskes | 518/700 |

FOREIGN PATENT DOCUMENTS

| | | |
|---|---|---|
| EP | 882 692 | 12/1998 |
| GB | 2092172 A | 11/1982 |
| WO | WO 97/36845 | 10/1997 |
| WO | WO 99/15482 | 4/1999 |
| WO | WO 00/32543 | 6/2000 |

OTHER PUBLICATIONS

Chinchen et al., The Methanol Synthesis: How Does It Work?, Chemtech, pp. 692–699 (Nov. 1990).

Dingler et al., Costs of Synthesis Gases and Methanol Part II, SRI International, Process Economics Program Review No. 87–3–1, Program Report No. 148 (Feb. 1983).

Kunii et al., Free Fall Reactor, Fluidization Engineering, Robert E. Krieger Publishing Co. NY, pp. 76–80 (1969).

Kuo, Evaluation of Direct Methane Conversion Processes, Chemical Reactor Technology for Environmentally Safe Reactors and Products, Kluwer Academic Publishers, pp. 183–226, (1993).

Meier et al., *Atlas of Zeolite Structural Types*, Butterworth Heineman, 4th ed., (1996).

Schlesinger et al., Fischer Tropsch Synthesis in Slurry Phase, Industrial and Engineering Chemistry, vol. 43, No. 6 pp. 1474–1479 (Jun. 1951).

Zenz et al., Fluidization and Fluid–Particle Systems, Reinhold Publishing Corp. NY, pp. 48–59 (1960).

"MTO—has its time come?" Nitrogen & Methanol, No. 246, (Jul.–Aug. 2000).

Barger et al., "Converting Natural Gas to Ethylene and Propylene by the UOP/Hydro MTO Process," 12th International Zeolite Conference Materials Research Society pp. 567–573 (1999).

Chang, "Methanol Conversion to Light Olefins," Catal. Rev.–Sci. Eng., 26(3&4), pp. 323–345 (1984).

Kaeding et al., "Production of Chemicals from Methanol," Journal of Catalysis 61, pp. 155–164 (1980).

Liang et al., "Characteristics and Performance of SAPO–34 Catalyst for Methanol–to–Olefin Conversion," Applied Catalysis, 64 pp. 31–40 (1990).

Marchi et al., "Catalytic Conversion of Methanol to Light Alkenes on SAPO Molecular Sieves," Applied Catalysis, 71 pp. 139–152 (1991).

* cited by examiner

METHANOL, OLEFIN, AND HYDROCARBON SYNTHESIS PROCESS

FIELD OF THE INVENTION

The invention relates to an improved method for the production of methanol, olefin, and hydrocarbons from a methane-containing gas, such as natural gas. In particular, the invention integrates a hydrocarbon synthesis unit with a methanol synthesis unit.

BACKGROUND

Methanol is a major chemical raw material. Present global consumption is about 27 million tons per year. Major uses of methanol include the production of acetic acid, formaldehyde, and methy-t-butylether. The latter, an oxygenate additive to gasoline, accounts for about a third of all use.

Worldwide demand for methanol is expected to increase as much as five fold over the next decade as potential new applications become commercialized. Such applications include the conversion of methanol to gas, such as the Mobil MTG Process, the conversion of methanol to light olefins, the use of methanol for power generation, and the use of methanol for fuel-cell powered automobiles.

Methanol synthesis is based on the equilibrium reactions of syngas, reactions (1) and (2).

$$CO + 2H_2 \leftrightarrows CH_3OH \quad (1)$$

$$CO_2 + 3H_2 \leftrightarrows CH_3OH + H_2O \quad (2)$$

Syngas is defined as a gas comprising primarily carbon monoxide (CO), carbon dioxide ($CO_2$) and hydrogen ($H_2$). Other gases present in syngas include methane ($CH_4$), and small amounts of light paraffins, such as ethane and propane. One way of characterizing the composition of a syngas stream for methanol synthesis is to account for the $CO_2$ present in the syngas stream. The syngas number (SN) is defined as follows:

$$SN = (H_2 - CO_2)/(CO + CO_2)$$

The forward reactions (1) and (2) are exothermic, that is, they result in the formation of net heat. Also, the forward reactions (1) and (2) generate less volumes of MeOH (gas) than the volumes of feed (gas) used to form the methanol. Therefore, to maximize methanol yields, i.e., force reactions (1) and (2) to the right, the process requires low temperatures and high pressures for high conversion. Still, a typical methanol reactor will convert only about 20% to 60% of the syngas fed to the reactor in a single pass through. To obtain higher conversions the unreacted syngas is separated from the product methanol and recycled back to the reactor or directed to a second reactor to produce additional methanol.

The initial step in the production of methanol is to produce syngas from a methane-containing gas, such as natural gas or refinery off-gas. The associated costs of producing the syngas accounts for over half of the capital investment in the methanol plant. The syngas can be generated using steam methane reforming or partial oxidation reforming, which includes combined reforming or autothermal reforming process.

UK Patent Application GB 2092172A recognizes that partial oxidation reformers used in the production of syngas for the production of synthetic hydrocarbons, that is, Fischer-Tropsch type conversion, often produces an excess quantity of $CO_2$ that eventually must be removed from the process stream. Consequently, associated costs in producing and removing the $CO_2$ exist. The UK Patent Application teaches that the excess $CO_2$ produced by the partial oxidation reformer can be utilized in part by first passing the syngas to a methanol synthesis reactor prior to the hydrocarbon synthesis reactor. The methanol synthesis utilizes the $CO_2$ as a carbon source to produce methanol according to reaction (2). Alternatively, the $CO_2$ can be mixed with hydrogen, produced from an external source, to convert the $CO_2$ to more CO according to the water-gas shift reaction. The additional CO is then used to produce more synthetic hydrocarbon.

U.S. Pat. No. 5,177,114 to Van Dijk et al. teaches the conversion of natural gas to methanol or methanol and synthetic hydrocarbons using a relatively low-cost, self-sufficient process. The natural gas is mixed with a 1:1 $O_2/N_2$ stream at elevated temperatures and pressures to produce a reform gas, which is then used to produce methanol and/or synthetic hydrocarbons. The natural gas is converted without the need for a costly steam reformer or a partial oxidation reformer. Also, the process is directed to low carbon conversions, e.g., about 50 to 65%, so that the tail gas from the process can be used to drive the compressors and other energy intensive units in the process.

It is very likely that the world demand for methanol will increase five-fold over the next decade. Methanol will be used as a chemical feedstock and as a competing fuel for transportation and power generation. As a result, processes designed to produce methanol in an economically efficient manner are highly desirable.

SUMMARY OF THE INVENTION

The invention integrates a methanol synthesis process with a hydrocarbon synthesis process. Particularly, the invention combines a syngas stream from a steam reformer with a syngas stream from a partial oxidation reformer to take advantage of their respective product syngas compositions. The invention utilizes most of the $CO_2$ and $H_2$ produced by the reformers. The hydrogen is used to convert the excess $CO_2$ to methanol and/or as an internal hydrogen source to further refine synthetic hydrocarbon. In the latter a portion of the hydrogen is separated from the first syngas stream or the recovered unreacted syngas stream, i.e., the recycle loop, and directed to a hydrocarbon synthesis refining unit. The combined syngas stream to the methanol reactor should have a SN of from 1.4 to 2.4, preferably of from 1.8 to 2.2.

In one embodiment, the invention further comprises separating a portion of $CO_2$ from a product gas from the hydrocarbon synthesis reactor to form a $CO_2$ containing gas and directing the $CO_2$ gas to a unit selected from the steam reformer, the methanol synthesis reactor, the partial oxidation reformer, or any combination thereof Preferably, the separated $CO_2$ is directed to the methanol synthesis reactor. In another embodiment, the invention further comprises directing a portion of the product gas from the hydrocarbon synthesis reactor without $CO_2$ separation to a unit selected from the steam reformer, the methanol synthesis reactor, the partial oxidation reformer, or any combination thereof The methanol synthesis reactor can be a low pressure reactor with an operating pressure from 200 psi to 700 psi or a conventional high pressure methanol synthesis reactor with an operating pressure from 500 psi to 2000 psi. The unreacted syngas from the methanol synthesis reactor can be separated from the methanol product and directed back to the methanol synthesis reactor, i.e., recycled, such that additional methanol can be produced. Alternatively, unreacted syngas can be directed to a secondary methanol synthesis reactor. In one embodiment, the methanol synthesis reactor will be a low pressure reactor, and the secondary methanol synthesis reactor a conventional high pressure reactor.

The produced methanol from the invention can be used to make olefins. In one embodiment, the produced methanol is first directed to a methanol refining unit where a portion of the water and other oxygenates are removed. The refined methanol is then used to make olefins, particularly ethylene and propylene. Preferably, a molecular sieve catalyst, more preferably a silicoaluminophosphate catalyst selected from SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, the metal containing forms thereof, and mixtures thereof, is used to convert the methanol to olefins.

BRIEF DESCRIPTION OF THE DRAWINGS

The present invention will be better understood by reference to the Detailed Description of the Invention when taken together with the attached drawings, wherein.

DETAILED DESCRIPTION OF THE INVENTION

Figure 1:
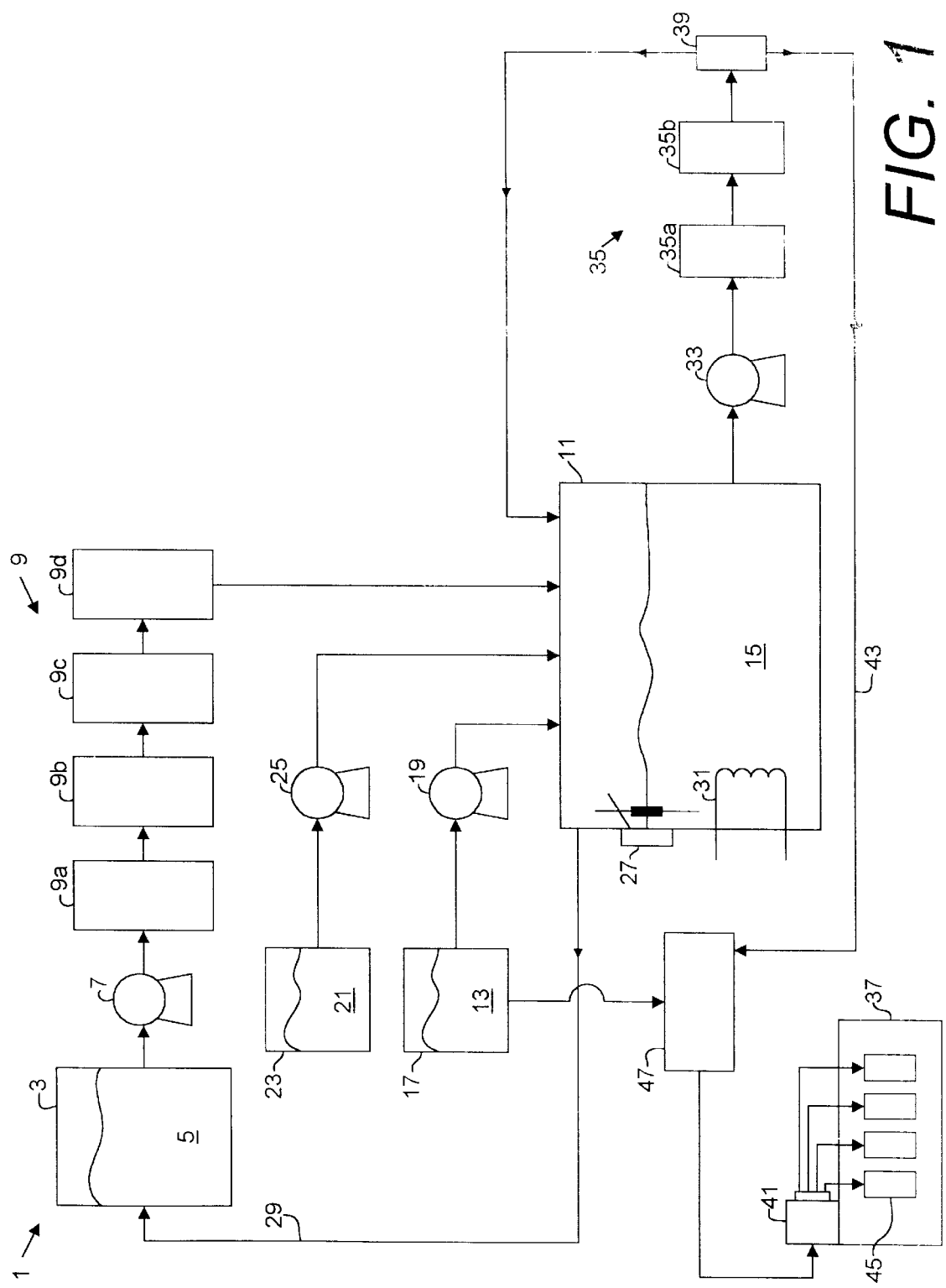
FIG. 1 is a schematic of an integrated methanol and hydrocarbon synthesis process.

This invention provides a method of making methanol and synthetic hydrocarbon by using an integrated plant design that results in lower capital and operating costs than two completely separated plants per unit of total products produced. Some of the cost savings are attributable to using the $CO_2$ produced by the syngas reformers and the hydrocarbon synthesis reactor to make additional methanol, reaction 2, and/or carbon monoxide, which is used to make synthetic hydrocarbon or methanol. Methanol production can be increased by the addition Of $CO_2$ to the methanol synthesis reactor or the syngas reformer if the SN is maintained at 2.0 to 2.1. Additional cost reductions come from integrating fuels, heating and cooling requirements, and the elimination or reduction of waste streams.

A steam reformer typically produces syngas with a SN of about 3, thus a steam reformer produces a significant amount of hydrogen that is not used for producing methanol. Steam reforming is the catalytic reaction of methane with steam to produce $H_2$ and CO, reaction (3). Significant amounts of $CO_2$ is also produced because the steam reacts with the CO according to the water-gas shift reaction (4) to produce $CO_2$ and $H_2$.

$$H_2O(g)+CH_4 \rightarrow 3H_2+CO \quad (3)$$

$$CO_2+H_2 \leftrightarrows CO+H_2O \quad (4)$$

The excess hydrogen builds up in the methanol synthesis recycle loop, thus increasing the cost of compressing the syngas prior to entering the methanol synthesis reactor. The cost of gas compression can be significant given the large throughput of feed to the methanol synthesis reactor. The process equipment would also require a larger volume capacity to accommodate the excess gas. One possible use for the excess hydrogen could be to refine crude stocks, but often, the methanol plant may not be located near to a refinery. This under utilization of the produced hydrogen is one of the disadvantages of using a steam reformer in a methanol synthesis plant.

Syngas can also be produced from methane by a catalytic oxidation process. An oxygen containing gas is fed into a reactor or reactor feed where it mixes with methane. The oxygen reacts with the methane to form CO, $CO_2$ and $H_2$. A typical oxidation reactor, more commonly referred to as partial oxidation (POX) reformer, will produce a syngas stream with a SN of 1.4 to 1.8. Although POX reformers are used to make methanol, much of the $CO_2$ produced by the POX reformers is not consumed during methanol synthesis due to the deficiency of hydrogen in the syngas feed. As a result, there is a loss of efficiency in the process of making methanol. This inefficiency is compounded in the process because when the $CO_2$ acts merely as a diluent, the $CO_2$ must be compressed along with the CO and $H_2$, and then eventually be removed from the system. This compression and removal of dilutent $CO_2$ adds to the cost of making methanol. In some cases, the $CO_2$ is released directly into the environment and therefor not used in any process.

The problems associated with excess $CO_2$ during methanol synthesis can be minimized if an inexpensive source of hydrogen was available. A SN greater than 2.0 is required if most of the $CO_2$ produced by the POX reformer is to be converted to methanol. One such source is the excess hydrogen produced by a steam reformer. For example, if a given amount of syngas from a steam reformer has a SN of 3.0 and an equal amount of syngas from a POX reformer has a SN of 1.8, then a combined syngas stream will have a SN of 2.4. The excess $H_2$ produced by the steam reformer is used to convert the excess $CO_2$ produced by the POX reformer into methanol. Therefore, a problem associated with a steam reformer, i.e., excess hydrogen, is combined with a problem associated with a POX reformer, i.e., waste $CO_2$, to produce additional methanol. What was once waste costs associated with the production of methanol are now transformed into more overall product for a given amount of natural gas feed.

To improve upon the overall efficiency of converting methane to methanol the portion of syngas that is not converted, i.e., unreacted syngas, is separated from the methanol product and directed to a secondary methanol synthesis reactor or recycled back to the methanol synthesis (MS) reactor. The MS reactor can be a conventional high pressure MS reactor operating at 500 psi to 2000 psi, or a low pressure MS reactor reactor operating at 200 psi to 700 psi. If only a single MS reactor is used in the process, the syngas not converted to methanol is separated from the methanol product and recycled back to the MS reactor feed. A portion of this recycle stream is purged to prevent the accumulation of inerts, i.e., methane or nitrogen, in the feed.

In some cases it may be cost effective to use two MS reactors in series. Preferably, the MS reactor will be a low pressure reactor, and the secondary MS reactor will operate at higher pressures. This will reduce the overall amount of syngas that would require compression to high pressures. Other embodiments may include using two low pressure MS reactors or two high pressure reactors.

The process of the invention also offers the flexibility to produce varied amounts of methanol and/or hydrocarbon. If there is greater demand for hydrocarbon product most of the syngas produced by the steam reformer can be directed to a hydrocarbon synthesis (HCS) reactor rather than the MS reactor. Having multiple HCS reactors in series can further increase the amount of hydrocarbon produced.

The product gas exiting the HCS reactor contains $CO_2$, steam, and some light paraffin. This product gas can be directed back to the steam reformer or to the MS reactor. Alternatively, it may be cost effective to separate a portion of the $CO_2$ from the product gas prior to directing the product gas back to the steam reformer or purging a portion of the product gas to remove inerts in the process. The separated $CO_2$ stream can then be directed to the MS reactor. Thus, the $CO_2$ and steam generated by the HCS process is not discarded, but used to make further product and/or syngas.

The advantages and cost efficiencies of using a steam reformer and a POX reformer is that the excess hydrogen produced from the steam reformer and the excess $CO_2$ produced from the POX reformer can be used to make additional methanol product. The $CO_2$ produced by the HCS process is also used to make methanol. Thus, there is little or no waste gas product in the invention that needs to be removed or discarded other than the light hydrocarbon product produced by both the MS process and the HCS process. However, this too can be used as a feed gas to heat the steam reformer or drive the compressors. The syngas from the POX reformer is variably combined with the syngas from the steam reformer to form a syngas stream with a SN of from 1.4 to 2.4, preferably of from 1.8 to 2.2.

For example, if the syngas from a steam reformer contains 20 units of $H_2$, 4 units of CO, and 2 units of $CO_2$, then SN=3, and there is an excess of hydrogen present to make methanol. In another example, if the syngas stream from a POX reformer contains 16 units of $H_2$, 8 units of CO, and 2 units of $CO_2$, then SN=1.4, and there is too little hydrogen present to make methanol from the available $CO_2$. The $CO_2$ will have to be purged from the process. A SN of about 2.1 is required to theoretically convert most if not all the $CO_2$ present in a syngas stream to methanol. However, in the example above if the syngas stream from the steam reformer is combined with the syngas from the POX reformer an SN of 2.0 is obtained.

The above sample calculation assumes that an equal amount of syngas from the steam reformer and the POX reformer are combined, that is, 26 units of gas from each. However, if the number of syngas units from the POX reformer is decreased in the combined feed to the MS reactor the SN ratio will increase. In a second example, only half of the syngas from the POX reformer is combined with the syngas from the steam reformer. The remaining half is directed to the HCS reactor to form hydrocarbon. As a result the syngas stream fed to the MS reactor will contain 28 units of $H_2$, 8 units of CO, and 3 units of $CO_2$. This will provide a SN of about 2.27. Thus, an optimal syngas feed is obtained and fed to the MS reactor. There is little or no excess hydrogen in the process. Nor is there any or little $CO_2$ that requires removal and release into the environment, since most of the $CO_2$ is used to produce methanol. The optimal syngas feed is then directed to the MS reactor. The portion of syngas that is not converted is separated from the methanol product and directed to a secondary MS reactor or recycled back to the MS reactor. In the former, the inerts and some of the unreacted syngas from the secondary MS reactor are then purged. In the latter, a portion of the recycled stream is purged to prevent the accumulation of inerts in the feed.

The steam reformer 6 can be of conventional design employing a commercial nickel catalyst such as, for example, that obtained from Katalco and designated as 23-1. The reactions take place inside tubular reactors, which are approximately 15 m long and are filled with catalyst. The tubular reactors are contained inside a combustion chamber. Steam reforming is highly endothermic, thus large amounts of heat must be supplied to the process. A portion of the natural gas is typically used as fuel to provide the necessary heat for the reaction. The pressure inside the tubes are typically 100 psia to 500 psia and the temperature at tube outlets is typically about 850° C. See, e.g., *Catalysis Science and Technology* Vol. 5, Chapter 1, J. R. Rostrup-Nielsen. The residence time of the gas stream inside the interior of the catalytic beds is about five seconds. The flow of input gases through the reactor catalyst bed should be approximately 300 lbs/hr/ft³ of catalyst. The commonly used catalyst in this process is Ni supported on a aluminum, magnesium, or silicon oxide.

Partial oxidation reforming is the preferred method of preparing syngas for producing methanol. Partial oxidation is the reaction of natural gas with controlled amounts of oxygen, reaction (5).

$$CH_4 + 1/2 O_2 \rightarrow CO + 2H_2 \tag{5}$$

However, in a commercial setting, this reaction is difficult to carry out as written. There will always be some production of water and carbon dioxide. Consequently, the actual SN is typically about 1.3 to 1.7. The presence of water and CO also provide the conditions necessary for the water-gas shift reaction to take place, reaction (4). As with the steam reformer, relatively high temperatures and low pressures favor production of syngas. However, once the reactants have been preheated, the reaction is self-sustaining without the need of additional heat. The process temperatures are typically 1250° C. to 1500° C., and the pressures range from 450 psia to 1800 psia. A preferred reactant ($O_2$:$CH_4$) mixture ratio of about 0.6 (by vol/vol) is typically used, and large amounts of $CO_2$ are produced.

The autothermal reformer combines partial oxidation and adiabatic steam reforming. In a first reaction zone, the methane is nearly completely converted to CO in a combustion type reaction, reaction (6). In a second reaction zone with a catalyst present, the methane reacts with steam to produce CO and $H_2$, reaction (7), as in a steam reformer. Equation 8 shows the theoretical syngas composition for an autothermal reformer, however because the water gas shift reaction is also occurring $CO_2$ is present in the output syngas stream. Some $CO_2$ is also produced in the combustion zone. The $CO_2$ is often recycled back to the reformer to optimize a select output syngas composition.

| $CH_4 + 3/2\ O_2$ | $\rightarrow$ | $CO + 2\ H_2O$ | (6) |
|---|---|---|---|
| $CH_4 + H_2O$ | $\rightarrow$ | $CO + 3\ H_2$ | (7) |
| $2\ CH_4 + 3/2\ O_2$ | $\rightarrow$ | $2\ CO + 3\ H_2 + H_2O$ | (8) |

An autothermal reformer produces syngas with a SN between 1.6 and 2.1.

The reactor for an autothermal reformer has a refractory lined pressure vessel with a specialized burner, a combustion chamber and a reaction chamber. The burner is an important element because it mixes the methane and oxygen in a turbulent diffusion flame. The flame core is often above 2000° C. Consequently, the burner must be designed so the heat from the flame core is transferred away from the burner. The catalysts used in the autothermal reformer are very similar to those used in a steam reformer. The reactor outlet temperature is typically about 900° C. to 1000° C. though as stated the temperature within the combustion zone is considerably higher. The reactor pressure is from 300 psi to 1200 psia.

Combined reforming combines an endothermic (heat is added), primary steam reformer with an exothermic (heat is released), secondary oxidation reformer. In the preferred design configuration, about half of the natural gas is fed to the steam reformer to produce a reformed gas. The reformed gas is then blended with the other half of natural gas and oxygen and introduced to an autothermal reformer. The advantage of combining the steam reformer with the autothermal reformer is that a SN of about 2 is obtained. Also, because the autothermal reformer merely functions as a secondary reformer oxygen consumption is decreased, thus lowering the costs of production. Combined reforming also permits higher operating pressures, which reduces compression energy requirements for the methanol synthesis feed.

One way of making a steam reformer economically competitive with a partial oxidation reformer in the production of methanol is to feed $CO_2$ to the steam reformer and/or to the produced syngas entering a methanol synthesis reactor. The addition of $CO_2$ has two effects on methanol synthesis. One, the $CO_2$ can react with the excess hydrogen produced in a steam reformer to produce more CO according to the well known water-gas shift reaction (4). The water-gas shift reaction provides a route to more CO if the $CO_2$ is directed to the steam reformer and/or the partial oxidation reformer. Two, the $CO_2$ in combination with the excess hydrogen can be used as a carbon source to produce more methanol if the SN is about 2.0 to 2.1. In theory, the addition of $CO_2$ to a combined steam reformer/methanol synthesis (SR/MS) process would make a SR/MS process economically competitive with a partial oxidation reformer/methanol synthesis. However, the unavailability of an on-site, clean, low cost $CO_2$ source presents a real world problem to the $CO_2$ solution.

For a recent study highlighting the value of adding $CO_2$ to a methanol synthesis process see, J. C. W. Kuo, *Chemical Reactor Technology for Environmentally Safe Reactors and Products,* p. 183–226, Kluwer Academic Publishers 1993; S. C. Nirula, SRI International, Process Economics Program PEP Review No. 87-3-1, October 1990. A report from SRI International, Process Economics Program Report No. 148 estimates a 15% decrease in the investment cost associated with steam reforming if $CO_2$ is used to produce methanol. The $CO_2$ can be reclaimed from flue gas, however because flue gas typically contains a significant concentration of contaminants, it is an impractical source of $CO_2$. Thus, if $CO_2$ is to be added to a steam reformer or a process syngas stream, a convenient, clean, virtually zero cost source is needed.

Referring to FIG. 1, a gas feedstock 2 comprising substantial amounts of methane, typically natural gas or a refinery off-gas is fed to a POX reformer 4 selected from an autothermal reformer or a fluidized bed syngas generator, preferably an autothermal reformer, and a steam reformer 6. An oxygen containing gas 8 is also fed to the POX reformer 4, and steam 3 is also fed to the steam reformer 6. The operating pressures and temperatures of the product gas stream 10 is from 300 psi to 1200 psi and 800° C. to 1100° C. if an autothermal reformer is used. Once the syngas is produced by the POX reformer the syngas may be cooled and/or purified. The treated or untreated syngas may then be used to produce a number of organic compounds, including methanol and hydrocarbon synthesis products. After exiting the POX reformer 4 syngas stream 10 can be directed toward the HCS reactor 12, the MS reactor 14 via stream 13, or a combination thereof The term "directed" when referring to a process stream of the invention means that the contents of the stated stream or portions thereof will eventually contact the stated process unit. Thus, portions of a stated process stream may be diverted from the stated process stream, or directed to a separation, purification, compression unit or combined with another process stream before contacting the stated process unit.

Often the natural gas source contains significant amounts of sulfur containing compounds which must be removed prior to entering the steam reformer and the partial oxidation reformer to prevent contamination of the reforming catalysts and the other process catalysts of the invention. Consequently, the methane containing gas is preferably stripped of most of the sulfur containing compounds before being introduced via stream 2 to the steam reformer 6 and the POX reformer 4. Any conventional equipment for this sulfur removing step can be utilized, such as a packed bed. Typically, a granular bed of zinc oxide such as 32-4 obtained from Katalco in ⅛ to 3/16 inch (3–5 mm) spheres can be used. System temperatures range between 200° C. and 500° C., and more preferably between 300° C. and 400° C. The space velocity through the bed should preferably be from 400 and 1000 standard cubic feet per hour per cubic feet of bed, and more preferably from 600 and 800 standard cubic feet per hour per cubic feet of bed.

In a conventional hydrocarbon synthesis process, liquid and gaseous hydrocarbon products are formed by contacting the $H_2$ and CO with a suitable Fischer-Tropsch type HCS catalyst. Suitable Fischer-Tropsch catalysts comprise, for example, one or more Group VIII catalytic metals such as Fe, Ni, Co, Ru, and Re. Typically, the catalyst comprises catalytically effective amounts of Co and one or more of Re, Ru, Fe, Ni, Th, Zr, Hf, U, Mg, La on a suitable inorganic support material, preferably one which comprises one or more refractory metal oxides. Preferred supports for cobalt-containing catalysts comprise titania, particularly when employing a slurry HCS process in which higher molecular weight, e.g., $C_{10}$ products, primarily paraffinic liquid hydrocarbon products are desired. The hydrocarbon products produced by an HCS process are typically upgraded to form suitable products such as, synthetic crude oil, liquid fuels (e.g., jet and diesel), a lubricating, industrial or medicinal oil, waxy hydrocarbons, olefins (by, e.g., catalytic cracking or steam cracking).

Many different Fischer-Tropsch reactor designs can be employed in the process of the present invention. One design is similar to that described in the article entitled Fischer-Tropsch Synthesis in Slurry Phase by M. D. Schlesinger, J. H. Crowell, Max Leva and H. H. Storch in *Engineering and Process Development,* Vol. 43, No. 6 (June, 1951) pp. 1474–1479. The article describes a synthesis reactor utilizing a precipitated iron catalyst suspended in a cooling oil. Such a reactor should be sized and operated under conditions to produce up to about 90% conversion of carbon monoxide into hydrocarbon products and carbon dioxide. The reactor used in this process should be operated at a pressure of from 100 psia to 500 psia at a temperature from 200° C. to 400° C. More preferably, the pressure should be from 150 psia to 300 psia at a temperature of from 240° C. to 300° C. A uniform distribution of synthesis feed gas uniformly across the reactor cross section is necessary to achieve good mixing between the rising gas bubbles and the slurry medium containing the dispersed catalyst particles. The gas distributor may consist of orifices or porous metal spargers. The preferred space velocity selected for optimal reactor conversion efficiency should be from 100 to 300 ft$^3$/hr/ft$^3$ of bed, preferably from 200 to 270 ft$^3$/hr/ft$^3$, and most preferably from 240 to 300 ft$^3$/hr/ft$^3$. The reactor diameter should be selected to give a feed superficial velocity (actual volumetric flow rate of feed gases divided by empty reactor cross-sectional area) between approximately 0.33 to 0.66 feet per second. The percent by weight of the foregoing iron catalyst is preferably from 5 to 15 percent by weight of iron in the slurry more preferably from 7.5 to 12.5 percent by weight and most preferably about 10% by weight of the slurry.

A heat exchanger within the slurry reactor is used to remove the large amounts of heat produced during hydrocarbon synthesis. The bubbling action in the slurry produces an efficient heat transfer medium for transferring the heat from the slurry to the heat exchanger. The preferred heat transfer medium is pressurized water introduced into the bottom of the tubes via concentric torroidal manifolds. The water undergoes boiling in the tubes which provides a large heat transfer coefficient. The efficient heat transfer from the slurry to the boiling water allows the slurry temperature to be nearly uniform throughout the reactor. The temperature of the slurry can be controlled by a combination of the height of water in the tubes and the steam pressure in the tubes. In the invention the steam generated in the HCS process can be directed to the steam reformer 6 via stream 3. Therefore, the costs of producing the steam is reduced.

Iron based catalysts are the preferred catalysts used in the slurry FT reactor due to their low cost. Most preferably, a precipitated iron catalyst is employed. Often specific amounts of alkali metal promoters are added to control the hydrocarbon product that is produced. Relatively large amounts of alkali metals will shift the product toward longer-chain molecules, while small amounts of alkali metal result in predominantly gaseous hydrocarbon product. Copper can also be added in small amounts as an induction promoter.

After a portion of the CO and H$_2$ is converted to hydrocarbon product 16 in the HCS reactor 12, the product gas 25 containing CO, H$_2$, CO$_2$, and H$_2$O (steam) is separated from the hydrocarbon product 16. The product gas 25 can be variably directed to the steam reformer 6 via stream 20, the POX reformer 4 via stream 21, and/or the MS reactor 14 via stream 22. A portion of the product gas 25 can also be purged to remove inerts in the process.

Alternatively, portions of the CO$_2$ can be separated from the product gas 25 with a CO$_2$ separator 18 to produce a gas with significantly higher proportions of CO$_2$. The CO$_2$ content of this gas can be as high as 95%, but more typically from 30% to 90%, more preferably from 50% to 80%. The CO$_2$ in gas stream 22 can then be variably directed to the steam reformer 6 via stream 20, the POX reformer 4 via stream 21, and/or the MS reactor 14 via stream 22 to produce a preselected ratio of CO$_2$ that enters the MS reactor 14. The concentration of CO$_2$ in stream 31 is also controlled by adjusting the operational parameters of the CO$_2$ separator 18. The remainder of the product gas 25 is purged to remove inerts from the process and/or directed back to the reformers.

One method of separating CO$_2$ from the product gas 25 is by using an aqueous potassium carbonate solution containing about 30% potassium carbonate. Stream 25 is bubbled through the carbonate solution at a temperature of from 80° C. to 150° C. Modifying the pressure of the stream will require optimizing the temperature and throughput for a given absorber size to achieve the same or similar desired reduction in the concentration of the carbon dioxide in the gas stream 25. The potassium carbonate solution containing the dissolved CO$_2$ is then heated in a separate vessel to drive off the absorbed carbon dioxide preferably at reduced pressure with steam stripping. The resulting stripped solution is then returned to the absorption vessel to absorb more carbon dioxide from stream 25. Other CO$_2$ extraction methods well known in the art can be employed in the invention.

The product 16 exiting the HCS reactor 12 comprises a variety of synfuels, including but not limited to C$_4$–C$_{20}$ parafins, C$_4$–C$_{20}$ olefins, aromatic hydrocarbons, unreacted syngas, and CO$_2$. Typically, long chain, paraffin waxes are produced in HCS reactor. These paraffinic products are then selectively converted to the desired hydrocarbon products by a hydrocarbon refining unit 40 at elevated hydrogen pressures with or without catalysts, FIG. 3. The refining units operate at hydrogen pressures of 500 psig to 3000 psig, and temperatures of about 300° C. to 600° C. The refining processes may include the hydrogenation of olefins and/or the hydrocracking/isomerization of the n-paraffins to iso-paraffins. The refined hydrocarbon products typically have excellent combustion properties and will often meet the stringent freeze point requirements of aviation fuel. Other potentially value products include detergent feedstocks, special solvents, lubricant feedstocks, and waxes.

One potential source of the hydrogen can be the steam reformer 6. At least a portion of the excess hydrogen produced by the steam reformer 6 can be separated by means known to one of ordinary skill in the art. The known separation methods include conventional cryogenic methods, membrane separations, and pressure swing absorption (PSA) unit. The process of separating the hydrogen from the steam reformer product stream 30 is depicted by hydrogen separator 36, FIG. 3. It is to be understood that the location of the hydrogen separator 36 can be positioned at other locations within the process of the invention, such as within the recycle stream 54.

Figure 2:
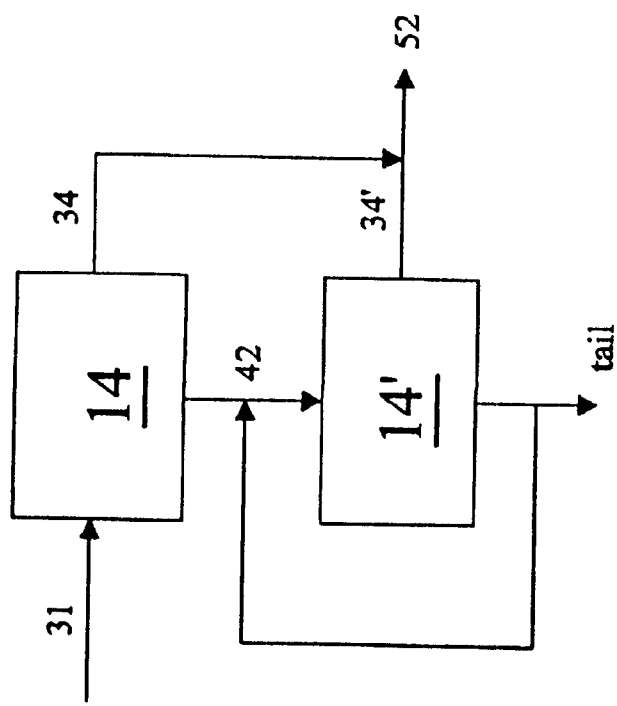
FIG. 2 is a schematic of the integrated process of FIG. 1 with multiple methanol synthesis reactors.
Figure 3:
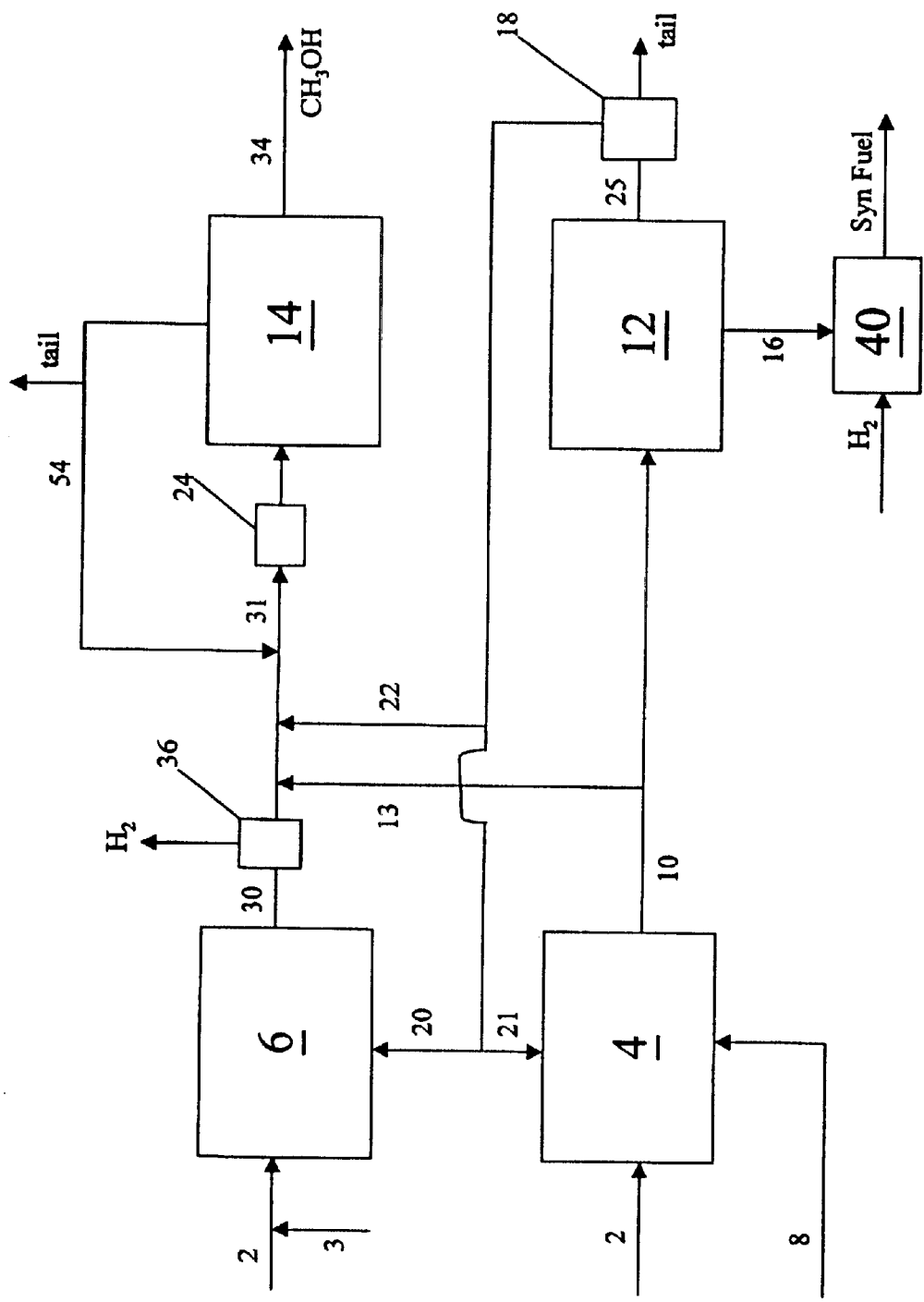
FIG. 3 is a schematic of an integrated process with a hydrogen separation unit and a hydrocarbon refining unit.

The MS reactor 14 is fed by the syngas stream 31. Syngas stream 31 comprises the syngas produced from the steam reformer 6 via stream 30, and the POX reformer 4 via stream 13, and optionally the recycle stream 54. Stream 31 may optionally comprise gas from the product gas 25 or the separated carbon dioxide stream 22 as shown in FIGS. 1 and 3. Syngas stream 31 will have a SN of from about 1.6 to 2.6, preferably from about 1.8 to 2.3. Generally, two types of methanol synthesis reactors can be used in the invention; a slurry type reactor or a conventional, fixed-bed reactor. The reactor operates at pressures between 200 psia and 2000 psia, and may require that the syngas stream 31 be compressed with a gas compressor 24 prior to entering the MS reactor 14. Because of the inherent low equilibrium conversions of reactions (1) and (2) the invention may include a recycle loop 54 containing recovered unreacted syngas from the MS reactor 14, as shown in FIG. 1. Alternatively, the invention may include one or more MS reactors in series as shown in FIG. 2. As shown in FIG. 2, the series of MS reactors minimizes or may eliminate the need to recycle the unreacted syngas by recycle stream 54. The unreacted syngas from MS reactor 14 is directed to a secondary MS reactor 14' via stream 42' to increase overall conversion efficiency without recycling.

In one embodiment, the MS reactor 14 is a liquid phase methanol reactor which converts a portion of the syngas stream 31 to methanol. The resultant methanol-containing syngas reactor effluent is cooled to condense the methanol, thereby producing a first methanol stream 34 and an unreacted syngas stream 54 in FIG. 1 and stream 42 in FIG. 2. Stream 54 is directed back to stream 31. The unreacted syngas stream 42 is directed to a conventional gas-phase MS reactor 14' to convert at least a portion of the unreacted syngas stream 42 to methanol, thereby forming a second methanol stream 34'. The unreacted gas, including inerts, are purged from a vent stream coming from the secondary MS reactor 14'. Both the first and second methanol streams 34, 34' are recovered as product or for further processing, as shown in FIG. 2. One advantage of using a low pressure MS reactor followed by a high pressure MS reactor is that less syngas requires compression to higher operating pressures because about half of the syngas is converted to methanol by the low pressure MS reactor.

The composition of stream 31 to the liquid phase MS reactor 14 can be any composition that is an acceptable feed to a conventional gas-phase methanol reactor. A typical composition would be 50–80% $H_2$, 10–30% CO, 5–20/$CO_2$, and 3–5% methane and other inerts, with a preferred SN ratio of from 1.4 to 2.4, preferably of from 1.8 to 2.2. Syngas streams with a SN ratio outside of this range can be processed by the invention, but the efficiency of the process will be lower. For example, if the SN falls below 1.8, the unconverted syngas would be difficult to process in the downstream gas phase MS reactor 14' because of the hydrogen deficiency. However, because of the large amounts of hydrogen produced by the steam reformer 6, sufficient amounts of hydrogen are nearly always available in the syngas stream 31.

The liquid phase MS reactor 14 can be any suitable reactor which is capable of converting a portion of the feed gas to methanol. Such reactors are described in U.S. Pat. Nos. 3,888,896 and 4,031,123 and Canadian Pat. No. 1,157,053. The reactor consists of an active methanol synthesis catalyst suspended in an inert hydrocarbon liquid, usually a mineral oil. The synthesis gas is bubbled through the catalyst-oil mixture where a portion of the $H_2$, CO and $CO_2$ is converted to methanol. Two operating modes can be used: the catalyst can be pellet-sized and fluidized by the inert liquid, or a powdered catalyst can be contained in the liquid, forming a slurry. Typically, the liquid phase MS reactor 14 operates at a pressure from 400 to 1200 psia, and the syngas stream 31, if not within this pressure range, is compressed by compressor 24. The reactor temperature can be from 150° C. to 400° C. with preferred temperatures from 230° C. to 250° C. The reactor space velocity in units of feed per hour per kilogram of catalyst is preferably from 4000 to 10,000 for the slurry mode reactor operation and from 2000 to 6000 for the fluidized mode. Since high single pass conversions are achievable in the liquid phase methanol reactor, the amount of syngas fed to the system can be increased significantly. As a result, methanol production levels can be increased without the large cost and equipment necessary to achieve such production levels with a single gas phase MS reactor and a recycling loop.

The catalyst used in the liquid phase reactor can be any known methanol-forming catalyst, such as those listed in Column 4 of U.S. Pat. No. 4,031,123. The particle sizes of the catalyst employed are known by those skilled in the art. Average particle sizes may range from 0.00002 to 0.25 inches, depending on the bed type (fixed, fluidized, or slurry) and liquid flow rate. By varying the catalyst composition as well as the reaction conditions in the reactor, higher aliphatic alcohols may be produced along with the methanol. The higher aliphatic alcohols may be condensed and recovered with the methanol as a combined product, or may be separated and recovered as an additional product.

As shown in FIG. 2, MS reactors 14 and 14' encompass a condensor/separator. Consequently, the methanol streams 34 and 34' and unreacted syngas streams 42 are shown exiting MS reactors 14 and 14', respectively as separated streams. In practice, the combined exiting streams would be directed to a separation tower or condensor to be separated. The reaction and separation processes are combined herein to simplify the process diagrams. The condensed methanol fraction is removed from the separator as a methanol product stream 34 and the unreacted syngas is removed as stream 42. Stream 42 is directed to a gas-phase MS reactor 14' to convert at least a portion of the syngas to methanol. Again, the methanol is condensed and separated to produce a second methanol stream 34' which is optionally combined with the first methanol stream 34 to form a single methanol product stream 52. The unreacted syngas can be recycled back to stream 31 or 42, and/or purged.

It is also to be understood that MS reactor 14 as shown in FIGS. 1–3 also encompass a condensor/separator. Consequently, the unreacted syngas stream 54 and methanol product stream 34 are shown exiting the MS reactor 14 as two separate streams. The HCS reactors depicted in FIGS. 1–3 also encompass a condensor/separator. Consequently, the unreacted syngas stream 25 and hydrocarbon product 16 are shown exiting the HCS reactor 12 as two separate streams.

In another embodiment of the invention, one or more "low pressure" MS reactors, similar to those developed by Imperial Chemical Industries is used. This process uses Cu/ZnO or Cu/ZnO/$Al_2O_3$ as a catalyst and operates from 200° C. to 300° C. at 50 to 110 atm. Methanol synthesis is carried out in the gas phase in a fixed bed reactor. It has been reported that all the MeOH is formed via $CO_2$ rather than CO as discussed by G. C. Chinchen, et al. in Chemtech. 692 (November 1990). The invention takes advantage of this fact by having sufficient amounts of low-cost, clean $CO_2$ available. The $CO_2$ is provided by the POX reformer 4 and stream 22. The power requirements, good catalyst life, larger capacity single-train convertor designs and improved reliability, of the low pressure technology result in lower energy consumption and economy of scale.

The methanol 34 produced in this invention can be directed to a methanol-to-olefin (MTO) conversion process. It may be desirable to first purify the methanol 34 prior to its use in the MTO process. In the methanol purification unit most of the water, methanol, and reaction by-products, such as ethers, other alcohols, aldehydes, ketones, etc., are removed in the condensate phase and fed to a three column distillation train. A first separation column operates at 49° C. and 130 psia overhead and separates light ends (mainly dimethyl ether). A second separation column, which separates half of the methanol product, operates at 127° C. and 110 psia overhead. The last column, which recovers the balance of the methanol, operates at 70° C. and 18 psia overhead. Higher alcohols are separated a few trays from the bottom and water is removed at the base of the column. LP steam provides the reboil energy for the first two columns and the vapor from the second column is condensed in the reboiler of the third column. The combined light ends and higher alcohols mixture are utilized as reformer furnace fuel.

One or more inert diluents may be present in the feedstock, for example, in an amount of from 1 to 99 molar percent, based on the total number of moles of all feed and diluent components fed to the reaction zone (or catalyst). As defined herein, diluents are compositions which are essentially non-reactive across a molecular sieve catalyst, and primarily function to make the methanol in the feedstock less concentrated. Typical diluents include, but are not necessarily limited to helium, argon, nitrogen, carbon monoxide, carbon dioxide, water, essentially non-reactive paraffins (especially the alkanes such as methane, ethane, and propane), essentially non-reactive alkylenes, essentially non-reactive aromatic compounds, and mixtures thereof The preferred diluents are water and nitrogen. Water can be injected in either liquid or vapor form.

Hydrocarbons can also be included as part of the feedstock, i.e., as co-feed. As defined herein, hydrocarbons included with the methanol are hydrocarbon compositions which are converted to another chemical arrangement when contacted with molecular sieve catalyst. These hydrocarbons can include olefins, reactive paraffins, reactive alkylaromatics, reactive aromatics or mixtures thereof Preferred hydrocarbon co-feeds include, propylene, butylene, pentylene, $C_4^+$ hydrocarbon mixtures, $C_5^+$ hydrocarbon mixtures, and mixtures thereof More preferred as co-feeds are a $C_4^+$ hydrocarbon mixtures, with the most preferred being $C_4^+$ hydrocarbon mixtures which are obtained from separation and recycle of reactor product.

In the MTO process of this invention, coked catalyst produced in the reactor can be regenerated by contacting the coked catalyst with a regeneration medium to remove all or part of the coke deposits. This regeneration can occur periodically within the reactor by ceasing the flow of feed to the reactor, introducing a regeneration medium, ceasing flow of the regeneration medium, and then reintroducing the feed to the fully or partially regenerated catalyst. Regeneration may also occur periodically or continuously outside the reactor by removing a portion of the deactivated catalyst to a separate regenerator, regenerating the coked catalyst in the regenerator, and subsequently reintroducing the regenerated catalyst to the reactor. Regeneration can occur at times and conditions appropriate to maintain a desired level of coke on the entire catalyst within the reactor.

Catalyst that has been contacted with feed in a reactor is defined herein as "feedstock exposed." Feedstock exposed catalyst will provide olefin conversion reaction products having substantially lower propane and coke content than a catalyst which is fresh and regenerated. A catalyst will typically provide lower amounts of propane as it is exposed to more feed, either through increasing time at a given feed rate or increasing feed rate over a given time.

Any standard reactor system, including fixed bed, fluid bed or moving bed systems, for the MTO reaction. Preferred reactors are co-current riser reactors and short contact time, countercurrent free-fall reactors. Desirably, the reactor is one in which an oxygenate feedstock can be contacted with a molecular sieve catalyst at a weight hourly space velocity (WHSV) of at least 1 $hr^{-1}$, preferably in the range of from 1 $hr^{-1}$ to 1000 $hr^{-1}$, more preferably in the range of from 20 $hr^{-1}$ to 1000 $hr^{-1}$, and most preferably in the range of from 20 $hr^{-1}$ to 500 $hr^{-1}$. WHSV is defined herein as the weight of oxygenate, and hydrocarbon which may optionally be in the feed, per hour per weight of the molecular sieve content of the catalyst. Because the catalyst or the feedstock may contain other materials which act as inerts or diluents, the WHSV is calculated on the weight basis of the oxygenate feed, and any hydrocarbon which may be present, and the molecular sieve contained in the catalyst.

Preferably, the oxygenate feed is contacted with the catalyst when the oxygenate is in a vapor phase. Alternately, the process may be carried out in a liquid or a mixed vapor/liquid phase. When the process is carried out in a liquid phase or a mixed vapor/liquid phase, different conversions and selectivities of feed-to-product may result depending upon the catalyst and reaction conditions.

The process can generally be carried out at a wide range of temperatures. An effective operating temperature range can be from 200° C. to 700° C., preferably from 300° C. to 600° C., more preferably from 350° C to 550° C. At the lower end of the temperature range, the formation of the desired olefin products may become markedly slow. At the upper end of the temperature range, the process may not form an optimum amount of product.

The conversion of oxygenates to produce light olefins may be carried out in a variety of catalytic reactors. Reactor types include fixed bed reactors, fluid bed reactors, and concurrent riser reactors as described in "Free Fall Reactor," *Fluidization Engineering,* D. Kunii and O. Levenspiel, Robert E. Krieger Publishing Co. New York, 1977, expressly incorporated herein by reference. Additionally, countercurrent free fall reactors may be used in the conversion process as described in U.S. Pat. No. 4,068,136 and "Riser Reactor", *Fluidization and Fluid-Particle Systems,* pages 48–59, F. A. Zenz and D. F. Othmo, Reinhold Publishing Corp., New York 1960, the detailed descriptions of which are also expressly incorporated herein by reference.

In a preferred embodiment of the continuous operation, only a portion of the catalyst is removed from the reactor and sent to the regenerator to remove the accumulated coke deposits that result during the catalytic reaction. In the regenerator, the catalyst is contacted with a regeneration medium containing oxygen or other oxidants. Examples of other oxidants include $O_3$, $SO_3$, $N_2O$, NO, $NO_2$, $N_2O_5$, and mixtures thereof. It is preferred to supply $O_2$ in the form of air. The air can be diluted with nitrogen, $CO_2$, or flue gas, and steam may be added. Desirably, the $O_2$ concentration in the regenerator is reduced to a controlled level to minimize overheating or the creation of hot spots in the spent or deactivated catalyst. The deactivated catalyst also may be regenerated reductively with $H_2$, CO, mixtures thereof, or other suitable reducing agents. A combination of oxidative regeneration and reductive regeneration can also be employed.

In essence, the coke deposits are removed from the catalyst during the regeneration process, forming a regenerated catalyst. The regenerated catalyst is then returned to the reactor for further contact with feed. Typical regeneration temperatures are from 250 to 700° C., desirably from 350 to 700° C. Preferably, regeneration is carried out at a temperature of 450 to 700° C.

It is desirable to strip at least some of the volatile organic components which may be adsorbed onto the catalyst or located within its microporous structure prior to entering the regenerator. This can be accomplished by passing a stripping gas over the catalyst in a stripper or stripping chamber, which can be located within the reactor or in a separate vessel. The stripping gas can be any substantially inert medium that is commonly used. Examples of stripping gas are steam, nitrogen, helium, argon, methane, $CO_2$, CO, flue gas, and hydrogen.

In one embodiment, the reactor and regenerator are configured such that the feed contacts the regenerated catalyst before it is returned to the reactor. In an alternative embodiment, the reactor and regenerator are configured such that the feed contacts the regenerated catalyst after it is returned to the reactor. In yet another embodiment, the feed stream can be split such that feed contacts regenerated catalyst before it is returned to the reactor and after it has been returned to the reactor.

The catalyst that is used in this invention is one that incorporates a silicoaluminophosphate (SAPO) molecular sieve. The molecular sieve comprises a three-dimensional microporous crystal framework structure of [$SiO_2$], [$AlO_2$] and [$PO_2$] corner sharing tetrahedral units. The way Si is incorporated into the structure can be determined by $^{29}$Si MAS NMR. See Blackwell and Patton, *J. Phys. Chem.*, 92, 3965 (1988). The desired SAPO molecular sieves will exhibit one or more peaks in the $^{29}$Si MAS NMR, with a chemical shift δ(Si) in the range of −88 to −96 ppm and with a combined peak area in that range of at least 20% of the total peak area of all peaks with a chemical shift δ(Si) in the range of −88 ppm to −115 ppm, where the δ(Si) chemical shifts refer to external tetramethylsilane (TMS).

It is preferred that the silicoaluminophosphate molecular sieve used in this invention have a relatively low $Si/Al_2$ ratio. In general, the lower the $Si/Al_2$ ratio, the lower the $C_{1-4}$ saturates selectivity, particularly propane selectivity. A $Si/Al_2$ ratio of less than 0.65 is desirable, with a $Si/Al_2$ ratio of not greater than 0.40 being preferred, and a $Si/Al_2$ ratio of not greater than 0.32 being particularly preferred. A $Si/Al_2$ ratio of not greater than 0.20 is most preferred.

Silicoaluminophosphate molecular sieves are generally classified as being microporous materials having 8, 10, or 12 membered ring structures. These ring structures can have an average pore size ranging from 3.5 to 15 angstroms. Preferred are the small pore SAPO molecular sieves having an average pore size of less than 5 angstroms, preferably an average pore size ranging from 3.5 angstroms to 5 angstroms, more preferably from 3.5 angstroms to 4.2 angstroms. These pore sizes are typical of molecular sieves having 8 membered rings.

In general, silicoaluminophosphate molecular sieves comprise a molecular framework of corner-sharing $[SiO_2]$, $[AlO_2]$, and $[PO_2]$ tetrahedral units. This type of framework is effective in converting various oxygenates into olefin products.

The $[PO_2]$ tetrahedral units within the framework structure of the molecular sieve of this invention can be provided by a variety of compositions. Examples of these phosphorus-containing compositions include phosphoric acid, organic phosphates such as triethyl phosphate, and aluminophosphates. The phosphorous-containing compositions are mixed with reactive silicon and aluminum-containing compositions under the appropriate conditions to form the molecular sieve.

The $[AlO_2]$ tetrahedral units within the framework structure can be provided by a variety of compositions. Examples of these aluminum-containing compositions include aluminum alkoxides such as aluminum isopropoxide, aluminum phosphates, aluminum hydroxide, sodium aluminate, and pseudoboehmite. The aluminum-containing compositions are mixed with reactive silicon and phosphorus-containing compositions under the appropriate conditions to form the molecular sieve.

The $[SiO_2]$ tetrahedral units within the framework structure can be provided by a variety of compositions. Examples of these silicon-containing compositions include silica soils and silicium alkoxides such as tetra ethyl orthosilicate. The silicon-containing compositions are mixed with reactive aluminum and phosphorus-containing compositions under the appropriate conditions to form the molecular sieve.

Substituted SAPOs can also be used in this invention. These compounds are generally known as MeAPSOs or metal-containing silicoaluminophosphates. The metal can be alkali metal ions (Group IA), alkaline earth metal ions (Group IIA), rare earth ions (Group IIIB, including the lanthanoid elements: lanthanum, cerium, praseodymium, neodymium, samarium, europium, gadolinium, terbium, dysprosium, holmium, erbium, thulium, ytterbium and lutetium; and scandium or yttrium) and the additional transition cations of Groups IVB, VB, VIB, VIIB, VIIIB, and IB.

Preferably, the Me represents atoms such as Zn, Mg, Mn, Co, Ni, Ga, Fe, Ti, Zr, Ge, Sn, and Cr. These atoms can be inserted into the tetrahedral framework through a $[MeO_2]$ tetrahedral unit. The $[MeO_2]$ tetrahedral unit carries a net electric charge depending on the valence state of the metal substituent. When the metal component has a valence state of +2, +3, +4, +5, or +6, the net electric charge is between −2 and +2. Incorporation of the metal component is typically accomplished adding the metal component during synthesis of the molecular sieve. However, post-synthesis ion exchange can also be used. In post synthesis exchange, the metal component will introduce cations into ion-exchange positions at an open surface of the molecular sieve, not into the framework itself Suitable silicoaluminophosphate molecular sieves include SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, the metal containing forms thereof, and mixtures thereof Preferred are SAPO-17, SAPO-18, SAPO-34, SAPO-35, SAPO-44, and SAPO-47, particularly SAPO-18 and SAPO-34, including the metal containing forms thereof, and mixtures thereof As used herein, the term mixture is synonymous with combination and is considered a composition of matter having two or more components in varying proportions, regardless of their physical state.

An aluminophosphate (ALPO) molecular sieve can also be included in the catalyst composition. Aluminophosphate molecular sieves are crystalline microporous oxides which can have an $AlPO_4$ framework. They can have additional elements within the framework, typically have uniform pore dimensions ranging from about 3 angstroms to about 10 angstroms, and are capable of making size selective separations of molecular species. More than two dozen structure types have been reported, including zeolite topological analogues. A more detailed description of the background and synthesis of aluminophosphates is found in U.S. Pat. No. 4,310,440, which is incorporated herein by reference in its entirety. Preferred ALPO structures are ALPO-5, ALPO-11, ALPO-18, ALPO-31, ALPO-34, ALPO-36, ALPO-37, and ALPO-46.

The silicoaluminophosphate molecular sieves are synthesized by hydrothermal crystallization methods generally known in the art. See, for example, U.S. Pat. Nos. 4,440,871; 4,861,743; 5,096,684; and 5,126,308, the methods of making of which are fully incorporated herein by reference. A reaction mixture is formed by mixing together reactive silicon, aluminum and phosphorus components, along with at least one template. Generally the mixture is sealed and heated, preferably under autogenous pressure, to a temperature of at least 100° C., preferably from 100° C. to 250° C., until a crystalline product is formed. Formation of the crystalline product can take anywhere from around 2 hours to as much as 2 weeks. In some cases, stirring or seeding with crystalline material will facilitate the formation of the product.

Typically, the molecular sieve product is formed in solution. It can be recovered by standard means, such as by centrifugation or filtration. The product can also be washed, recovered by the same means, and dried.

As a result of the crystallization process, the recovered sieve contains within its pores at least a portion of the template used in making the initial reaction mixture. The crystalline structure essentially wraps around the template, and the template must be removed so that the molecular sieve can exhibit catalytic activity. Once the template is removed, the crystalline structure that remains has what is typically called an intracrystalline pore system.

In many cases, depending upon the nature of the final product formed, the template may be too large to be eluted from the intracrystalline pore system. In such a case, the template can be removed by a heat treatment process. For example, the template can be calcined, or essentially combusted, in the presence of an oxygen-containing gas, by contacting the template-containing sieve in the presence of the oxygen-containing gas and heating at temperatures from 200° C. to 900° C. In some cases, it may be desirable to heat in an environment having a low oxygen concentration. In these cases, however, the result will typically be a breakdown of the template into a smaller component, rather than by the combustion process. This type of process can be used for partial or complete removal of the template from the intracrystalline pore system. In other cases, with smaller templates, complete or partial removal from the sieve can be accomplished by conventional desorption processes such as those used in making standard zeolites.

The reaction mixture can contain one or more templates. Templates are structure directing or affecting agents, and typically contain nitrogen, phosphorus, oxygen, carbon, hydrogen or a combination thereof, and can also contain at least one alkyl or aryl group, with 1 to 8 carbons being present in the alkyl or aryl group. Mixtures of two or more templates can produce mixtures of different sieves or predominantly one sieve where one template is more strongly directing than another.

Representative templates include tetraethyl ammonium salts, cyclopentylamine, aminomethyl cyclohexane, piperidine, triethylamine, cyclohexylamine, tri-ethyl hydroxyethylamine, morpholine, dipropylamine (DPA), pyridine, isopropylamine and combinations thereof Preferred templates are triethylamine, cyclohexylamine, piperidine, pyridine, isopropylamine, tetraethyl ammonium salts, dipropylamine, and mixtures thereof The tetraethylammonium salts include tetraethyl ammonium hydroxide (TEAOH), tetraethyl ammonium phosphate, tetraethyl ammonium fluoride, tetraethyl ammonium bromide, tetraethyl ammonium chloride, tetraethyl ammonium acetate. Preferred tetraethyl ammonium salts are tetraethyl ammonium hydroxide and tetraethyl ammonium phosphate.

The SAPO molecular sieve structure can be effectively controlled using combinations of templates. For example, in a particularly preferred embodiment, the SAPO molecular sieve is manufactured using a template combination of TEAOH and dipropylamine. This combination results in a particularly desirable SAPO structure for the conversion of oxygenates, particularly methanol and dimethyl ether, to light olefins such as ethylene and propylene.

The silicoaluminophosphate molecular sieve is typically admixed (i.e., blended) with other materials. When blended, the resulting composition is typically referred to as a SAPO catalyst, with the catalyst comprising the SAPO molecular sieve.

Materials which can be blended with the molecular sieve can be various inert or catalytically active materials, or various binder materials. These materials include compositions such as kaolin and other clays, various forms of rare earth metals, metal oxides, other non-zeolite catalyst components, zeolite catalyst components, alumina or alumina sol, titania, zirconia, magnesia, thoria, beryllia, quartz, silica or silica or silica sol, and mixtures thereof These components are also effective in reducing, inter alia, overall catalyst cost, acting as a thermal sink to assist in heat shielding the catalyst during regeneration, densifying the catalyst and increasing catalyst strength. It is particularly desirable that the inert materials that are used in the catalyst to act as a thermal sink have a heat capacity of from 0.05 cal/g-° C. to 1 cal/g-° C., more preferably from 0.1 cal/g-° C. to 0.8 cal/g-° C., most preferably from 0.1 cal/g-° C. to 0.5 cal/g-° C.

Additional molecular sieve materials can be included as a part of the SAPO catalyst composition or they can be used as separate molecular sieve catalysts in admixture with the SAPO catalyst if desired. Structural types of small pore molecular sieves that are suitable for use in this invention include AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof Structural types of medium pore molecular sieves that are suitable for use in this invention include MFI, MEL, MTW, EUO, MTT, HEU, FER, AFO, AEL, TON, and substituted forms thereof These small and medium pore molecular sieves are described in greater detail in the *Atlas of Zeolite Structural Types,* W. M. Meier and D. H. Olsen, Butterworth Heineman, 3rd ed., 1997, the detailed description of which is explicitly incorporated herein by reference. Preferred molecular sieves which can be combined with a silicoaluminophosphate catalyst include ZSM-5, ZSM-34, erionite, and chabazite.

One skilled in the art will also appreciate that the olefins produced by the MTO process of the present invention can be polymerized to form polyolefins, particularly polyethylene and polypropylene. Processes for forming polyolefins from olefins are known in the art. Catalytic processes are preferred. Particularly preferred are metallocene, Ziegler/Natta and acid catalytic systems. See, for example, U.S. Patent Nos. 3,258,455; 3,305,538; 3,364,190; 5,892,079; 4,659,685; 4,076,698; 3,645,992; 4,302,565; and 4,243,691, the catalyst and process descriptions of each being expressly incorporated herein by reference. In general, these methods involve contacting the olefin product with a polyolefin-forming catalyst at a pressure and temperature effective to form the polyolefin product.

A preferred polyolefin-forming catalyst is a metallocene catalyst. The preferred temperature range of operation is from 50° C. to 240° C. and the reaction can be carried out at low, medium or high pressure, being anywhere within the range of 1 bar to 200 bars. For processes carried out in solution, an inert diluent can be used, and the preferred operating pressure range is from 10 bars to 150 bars, with a preferred temperature range of from 120° C. to 230° C. For gas phase processes, it is preferred that the temperature generally be from 60° C. to 160° C., and that the operating pressure be from 5 bars to 50 bars.

The present invention is a highly flexible process with regards to the proportional amounts of methanol or synthetic hydrocarbon that may be produced. If more methanol product is desired, amount of syngas diverted to stream 13 and from stream 10 the can be increased accordingly. Alternatively, multiple methanol synthesis reactors may be operated in series since the capital investment of such reactors is minimal compared to the cost of the syngas reformers. Similarly, if more hydrocarbon product is desired the invention can be modified to affect such a result.

Having now fully described this invention, it will be appreciated by those skilled in the art that the invention can be performed within a wide range of parameters within what is claimed, without departing from the spirit and scope of the invention.

We claim:

1. A method for making methanol comprising:
    directing a methane containing gas and steam to a steam reformer to form a first syngas stream and directing at least a portion of the first syngas stream to a methanol synthesis reactor;

directing a methane containing gas and oxygen to a partial oxidation reformer to form a second syngas stream and directing at least a portion of the second syngas stream to the methanol synthesis reactor; and directing at least a portion of the second syngas stream to a hydrocarbon synthesis reactor;

wherein the portions of the first and the second syngas streams directed to the methanol synthesis reactor yield a combined syngas stream having a syngas number of from 1.4 to 2.6.

2. The method of claim 1 further comprising separating a portion of carbon dioxide from a product gas from the hydrocarbon synthesis reactor to form a carbon dioxide gas and directing the carbon dioxide gas to a unit selected from the steam reformer, the methanol synthesis reactor, the partial oxidation reformer, or any combination thereof.

3. The method of claim 1 further comprising directing a portion of a product gas from the hydrocarbon synthesis reactor to a unit selected from the steam reformer, the methanol synthesis reactor, the partial oxidation reformer, or any combination thereof.

4. The method of claim 1 further comprising recovering unreacted syngas from the methanol synthesis reactor and directing at least a portion of the recovered gas to the methanol synthesis reactor.

5. The method of claim 1 further comprising separating at least a portion of hydrogen from the first syngas stream and directing the separated hydrogen to a hydrocarbon synthesis refining unit.

6. The method of claim 4 further comprising separating at least a portion of hydrogen from the recovered syngas stream and directing the separated hydrogen to a hydrocarbon synthesis refining unit.

7. The method of claim 1 further comprising directing methanol from the methanol synthesis reactor to a methanol refining unit.

8. The method of claim 7 further comprising directing at least a portion of methanol from the methanol refining unit to an oxygenate conversion reactor, wherein at least a portion of the methanol in contact with a catalyst is converted to a product including olefin.

9. The method of claim 8 wherein the catalyst comprises a molecular sieve catalyst.

10. The method of claim wherein the molecular sieve catalyst comprises a silicoaluminophosphate molecular sieve selected from SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAP42, SAPO-44, SAPO-47, SAPO-56, the metal containing forms thereof, or mixtures thereof.

11. A method for making methanol comprising:

directing a methane containing gas and steam to a steam reformer to form a first syngas stream and directing at least a portion of the first syngas stream to a methanol synthesis reactor;

directing a methane containing gas and oxygen to a partial oxidation reformer to form a second syngas stream and directing at least a portion of the second syngas stream to the methanol synthesis reactor;

directing at least a portion of the second syngas stream to a hydrocarbon synthesis reactor; and recovering unreacted syngas from the methanol synthesis reactor and directing at least a portion of the recovered gas to a secondary methanol synthesis reactor;

wherein the portions of the first and the second syngas streams directed to the methanol synthesis reactor yield a combined syngas stream having a syngas number of from 1.4 to 2.6.

12. The method of claim 11 further comprising separating a portion of carbon dioxide from a product gas from the hydrocarbon synthesis reactor to form a carbon dioxide gas and directing the carbon dioxide gas to a unit selected from the steam reformer, the methanol synthesis reactor, the partial oxidation reformer, or any combination thereof.

13. The method of claim 11 further comprising directing a portion of a product gas from the hydrocarbon synthesis reactor to a unit selected from the steam reformer, the methanol synthesis reactor, the partial oxidation reformer, or any combination thereof.

14. The method of claim 11 wherein the methanol synthesis reactor comprises a low pressure reactor with an operating pressure from 200 psi to 700 psi and the secondary methanol synthesis reactor comprises a reactor with an operating pressure from 500 psi to 2000 psi.

15. The method of claim 11 further comprising separating at least a portion of hydrogen from the first syngas stream and directing the separated hydrogen to a hydrocarbon synthesis refining unit.

16. The method of claim 11 further comprising directing methanol from the methanol synthesis reactor and the secondary methanol synthesis reactor to a methanol refining unit.

17. The method of claim 16 further comprising directing at least a portion of methanol from the methanol refining unit to an oxygenate conversion reactor, wherein at least a portion of the methanol in contact with a catalyst is converted to a product including olefin.

18. The method of claim 17 wherein the catalyst comprises a molecular sieve catalyst.

19. The method of claim 18 wherein the molecular sieve catalyst comprises. a silicoaluminophosphate molecular sieve selected from SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, the metal containing forms thereof, or mixtures thereof.

20. The method of claim 1 wherein the combined syngas stream is maintained at the syngas number of from 1.8 to 2.6 by varying the portion of the second syngas stream that is directed to the methanol synthesis reactor.

21. The method of claim 11 wherein the combined syngas stream is maintained at the syngas number of from 1.8 to 2.6 by varying the portion of the second syngas stream that is directed to the methanol synthesis reactor.

* * * * *